(12) United States Patent
Merkel et al.

(10) Patent No.: US 7,057,743 B2
(45) Date of Patent: Jun. 6, 2006

(54) DEVICE, METHOD AND SYSTEM FOR MEASURING THE DISTRIBUTION OF SELECTED PROPERTIES IN A MATERIAL

(75) Inventors: Harald Merkel, Källered (SE); Mikael Reimers, Västra Frölunda (SE)

(73) Assignee: Frigoscandia Equipment AB, Helsingborg (SE)

( * ) Notice: Subject to any disclaimer, the term of this patent is extended or adjusted under 35 U.S.C. 154(b) by 1014 days.

(21) Appl. No.: 09/885,285

(22) Filed: Dec. 4, 2000

(65) Prior Publication Data

US 2003/0024315 A1   Feb. 6, 2003

(30) Foreign Application Priority Data

Aug. 31, 2000 (SE) .................................. 0003078

(51) Int. Cl.
  *G01B 11/24* (2006.01)
  *G01N 21/00* (2006.01)
  *G01N 29/00* (2006.01)
  *G01N 21/86* (2006.01)
  *G01N 9/04* (2006.01)
  *G06K 9/00* (2006.01)
  *G01R 27/32* (2006.01)

(52) U.S. Cl. .................... 356/601; 356/73; 382/154; 73/602; 250/559.22; 250/223 R; 324/637; 324/640

(58) Field of Classification Search .............. 356/601, 356/73, 238.1–238.3, 239.1–239.8, 237.2, 356/429–431; 324/600, 71.1, 629–630, 633–635, 324/637–640, 642–644, 691–695; 73/30.01, 73/53.01, 602, 634, 23.2, 23.28, 29.01; 600/309, 600/310, 402, 425, 430, 437–461, 473–480
See application file for complete search history.

(56) References Cited

U.S. PATENT DOCUMENTS

| 4,798,209 A | * | 1/1989 | Klingenbeck et al. | ...... 600/430 |
| 5,588,032 A | * | 12/1996 | Johnson et al. | ................ 378/8 |
| 6,006,128 A | * | 12/1999 | Izatt et al. | .................. 600/476 |
| 6,026,173 A | * | 2/2000 | Svenson et al. | ............ 382/131 |

FOREIGN PATENT DOCUMENTS

WO   WO 98/01069   1/1998

* cited by examiner

*Primary Examiner*—Gregory J. Toatley, Jr.
*Assistant Examiner*—Gordon J. Stock, Jr.
(74) *Attorney, Agent, or Firm*—Birch, Stewart, Kolasch & Birch, LLP

(57) ABSTRACT

The present invention relates to a device for measuring the distribution of selected properties of materials, said device comprises an emitter of electromagnetic radiation and furthermore at least one sensor of a first type. The emitter emits electromagnetic radiation in a selected frequency range towards said materials and a sensor of the first type detects electromagnetic radiation in a selected frequency range coming from said materials. The detected electromagnetic radiation having been emitted by said emitter. The device also comprises means to generate a three dimensional image contour information regarding the said material's position in space, and an analyser which (a) receives information from said sensors and (b) processes this information and (c) generates signals containing information about the distribution of said properties as output. The invention also relates to a system and a method for measuring the distribution of selected properties of materials.

8 Claims, 4 Drawing Sheets

DEVICE, METHOD AND SYSTEM FOR MEASURING THE DISTRIBUTION OF SELECTED PROPERTIES IN A MATERIAL

FIELD OF INVENTION

This invention relates to a device for measuring the distribution of selected properties in a material, and in particular a device that non-contacting and non-destructively measures the spatial distribution of material properties, such as density, water contents and temperature of materials, by detecting electromagnetic radiation. The invention also relates to a method and a system.

BACKGROUND OF THE INVENTION

Many industrial processes depend on the measurement of material properties as temperature, water contents and material density. A close monitoring of these material properties results often in increased efficiency and improved product quality. Additional benefits are likely to occur, if such measurements can be accomplished fast and in a non-destructive, non-invasive, and non-contacting way with acceptable accuracy.

As an example the determination of the temperature distribution in foodstuff during heating process. Here, an on-line monitoring of the temperature distribution helps to avoid cold spots where bacteria are not eliminated completely or to reduce the overdue heating time spent to ensure complete bacteria elimination. This results in a reduced heating time and reduced energy consumption as well as in an increased throughput of the production line.

Material properties are traditionally measured by some form of destruction (sample separation, peeking) but can often be measured by the analysis of transmitted electromagnetic radiation by evaluating the dielectric response of the material. Measurements using electromagnetic radiation are generally contact-free and non-destructive.

A suitable frequency region of electromagnetic radiation to determine material properties as temperature distribution, water contents and density is the lower microwave region where water absorption is not too large and the wavelength is already short enough to ensure reasonable spatial resolution. The determination of the above material properties is achieved by analysing the dielectric response of the material based on the material's polarisability. Dielectric data of a material sample are typically obtained in analysing the electromagnetic wave's reflection and transmission properties or a combination of both. In order to obtain a distribution of the material properties, a three-dimensional image of the material's dielectric response must be measured. This requires to move the microwave detector setup and the material sample relative to each other.

Prior art instruments make use of either a single measurement frequency or the emission frequency is swept within a frequency interval (FMCW) and the average delay time is calculated from the obtained data.

Prior art that approaches to dielectric imaging, use the transmission of electromagnetic radiation of a single frequency (or a small band) between a multitude of antenna locations or the material sample is shifted and rotated or shifted in two dimensions in order to obtain a spatial resolution. Based on these data the dielectric image is obtained e.g. by the well-known CSI (contrast source iteration) method where the location and strength of polarisation sources are obtained in an iterative process.

Using techniques well-known to a skilled person (i.e. Contrast Source Iteration CSI, as described below) the electromagnetic picture is used to calculate the unknown dielectric functions in the dielectric picture.

Starting from Maxwell's Equations (as described by R. F. Harrington, in the book with the title "Time Harmonic Electromagnetic Fields", published by Mc. Graw Hill 1961) one assumes that any region where the dielectric function is different from unity, the electromagnetic field creates bound charges due to polarisation. These bound charges are created by the electric field itself and they oscillate with it resulting in an additional current component:

$$j(p) = \epsilon(p) \cdot u(p)$$

where the current density is j, the electric field is u and the dielectric function of the material is $\epsilon$ and of the background is denoted $\epsilon_b$. Assume p and q to be two position vectors in a two dimensional cross section of the measurement gap. D is a domain which contains the cross section of the material sample. The vector q denotes the source point of the electromagnetic radiation. Based on that a general relation for the connection between the electric fields in the measurement space is obtained formally by applying the definition of a Green's function for the electric current:

$$u_j(p) = k^2 \int_D G(p,q) \cdot j(q) \cdot dv(q)$$

Inserting the above current density relation and splitting the integral yields:

$$u_j(p) = k^2 \int_D G(p,q) \cdot \epsilon_b \cdot u(p) \cdot dv(q) + k^2 \int_D G(p,q) \cdot [\epsilon(p) - \epsilon_b] \cdot u(p) \cdot dv(q)$$

Here the first term denotes the electric field when the dielectric response of the background is present only, the second term stands for the fields generated by polarisation i.e. a dielectric contrast. The fields when only a background is presented are referred to as incident fields $u^{inc}$. Then the field at an observation point incident from the radiation source is (according to an article by P. M. van den Berg, B. J. Kooj, R. E. Kleinman, with the title "Image Reconstruction from Iswich-Data III", published in IEEE Antenna and Propagation Magazine, Vol.41 No.2 April 1999, p. 27–32):

$$u_j(p) = u_j^{inc}(p) + k^2 \int_D G(p,q) \cdot \chi(q) \cdot u_j(q) \cdot dv(q)$$

where G denotes the two-dimensional Green's function of the electromagnetic problem $$G(p,q) = \frac{i}{4} H_0^{(i)}(k \cdot |p-q|)$$

and the polarisability function $\chi$ depends on the dielectric function of the material $\epsilon$ and the background $\epsilon_b$ in the following way:

$$\chi(p) = \frac{\varepsilon(p) - \varepsilon_b}{\varepsilon_0}$$

Defining scattered fields f one obtains directly:

$$F_j(r) = u_j(r) - u_j^{inc}(r) = k^2 \int_D G(r, q) \cdot \chi(q) \cdot u_j(q) \cdot dv(q)$$

From this an integral equation for the scattered electric field at any point r is set up.

$$F_j(r) = \frac{i}{4} k^2 \int_D H_0^{(i)}(k \cdot |r - q|) \cdot \chi(q) \cdot [F_j(q) + u_j^{inc}(q)] \cdot dv(q)$$

This relation is fulfilled exactly when r is equal to the antenna location and the $F_i(r)$ are measured values of the scattered fields for a given wave vector k for a frequency f:

$$k = \frac{2\pi}{c} \cdot f.$$

The values of $F_i(r)$ for the points interior to the region D are only fulfilled approximately. So the above relation has to be solved for a set K of k vectors and a set Q of internal points resulting in a [K·Q]×[K·Q] non-linear matrix problem for the fields $F_i(r)$ and the polarisabilities $\chi(r)$.

In matrix form the state equation becomes:

$$u = u^{inc} + G\chi u$$

whereas the frequency relation is:

$$F = G\chi u$$

Introducing the contrast source $\phi = \chi \cdot u$ the above relations become $\phi = \chi u^{inc} + \chi G\phi$ at all Q interior points, for any of the K measurement frequencies $F = G\phi$ at a single antenna location, for any of the K measurement frequencies Using the method of conjugated gradients sequences for the contrasts and the contrast sources solving the above problem are obtained.

OBJECTIVE OF THE INVENTION

A device has been designed to measure the spatial distribution of the temperature, water contents and density distribution in a material based on the dielectric and magnetic information contained in transmission measurements obtained using microwave radiation.

This invention covers two methods to resolve such information from measured data:

(a) The temperature, density and water contents profile can be obtained by interpolation between a set of previously measured material samples where the profiles are known in advance. There the measurement result is found by a best fit to the interpolation database.

(b) The said profile is found by direct calculation of the inverse scattering problem resulting in a known distribution of the dielectric and magnetic properties. Based on models on the dependence of the dielectric and magnetic properties as functions of the wanted parameters, a map of the said properties is obtained directly.

The instrument proposed here may only use one mechanical scanning dimension. Due to the usage of a multi-channel antenna and a multitude of frequencies, a two-dimensional cross-section of the dielectric picture is obtained. This calculation process involves a novel method related to contrast source iteration where the location and strength of polarisation sources are obtained in an iterative process based on transmitted electromagnetic field measurements at a multitude of frequencies. Thereby the antenna patterns must be frequency dependent and they are assumed to be directed in cross section of the sample allowing an essentially two dimensional approach.

In order to facilitate the calculation of the dielectric parameters, regions where the dielectric properties are at first order constant are obtained by an e.g. evaluating video pictures taken from at least two different points of view with overlapping image region. From these video pictures a reasonable guess of the material sample's dielectric structure is made. As an alternative ultrasound images can be used for the same purpose or a three dimensional image of the material sample may be stored in a memory.

SUMMARY OF THE INVENTION

The object with the invention is thus to provide a device that measures the spatial property distribution in a non-contacting and non-destructive way.

An advantage of the invention is that it provides on-line fast measurements of spatially resolved material parameter distributions by means of a combined application of microwave reflection and transmission measurements and a three dimensional contour of the material.

Traditionally the temperature and density of the material samples is obtained by probing a certain fraction of the material samples. This method allows a complete on-line monitoring of all material samples in production increasing the degree of product control.

The accuracy of the measurement is checked by means of calibration samples with known constituents and known temperature profile which are measured at regular intervals. Thereby it is sufficient to perform invasive temperature measurements after the sample has been measured at different points of the sample and compare them to the instrument's findings. As a additional verification process the same procedure can be repeated when the sample has e.g. cooled down.

Summarising the advantages of this invention it provides a non-destructive, non-invasive and non-contacting, fast and automatic measurement process of the water contents and temperature distribution of dielectric bodies requiring minimal human intervention. The measurement process is insensitive to changes in product size, form and positioning.

Other features of the current invention will become more apparent in the following detailed description of the preferred embodiment which by means of example illustrate the principles of this invention.

DETAILED DESCRIPTION OF PREFERRED EMBODIMENTS

Figure 1:
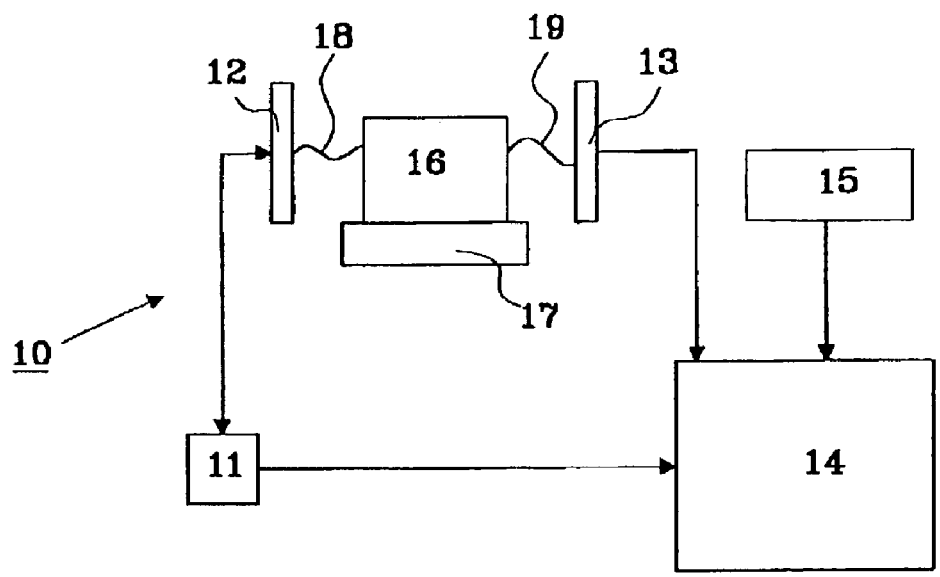
FIG. 1 is a schematic diagram of a first embodiment of a device according to this invention.

As shown in FIG. 1 the primary elements of a measurement device 10 according to a first embodiment of the present invention are a microwave generator 11, a transmitting antenna 12, a receiving antenna 13, an analyser 14. These elements work together to analyse the distribution of material properties (such as water contents, density and temperature) in a material sample 16. The sample is carried on a conveyor means 17, which may consist of a slide table mounted on a linear motor, and is arranged in a measurement gap between said transmitting antenna 12 and receiving antenna 13.

The generator 11 is connected to the transmitting antenna 12 and generates electromagnetic radiation, which is transmitted from the transmitting antenna 12 towards the receiving antenna 13. The material sample 16 is placed between said transmitting antenna 12 and said receiving antenna 13, which indicate that at least a part of the transmitted radiation passed through the material sample 16. The electromagnetic radiation is transmitted in the form of signals 18, each having a first amplitude and phase, and a different frequency within a frequency range.

The generator 11 is also connected to the analyser 14, and information regarding the amplitude and frequency of each transmitted signal 18 is sent to the analyser 14.

The transmitted signals 18 pass, at least partially, through the material sample 16 and are received by the receiving antenna 13 as receiving signals 19 each having a second amplitude and phase, which may be different from the first amplitude and phase, for each different frequency.

The receiving antenna 13 is connected to the analyser 14, which receives information regarding the received signals 19. The analyser 14 compares the amplitude and phase of the transmitted signal with the corresponding amplitude and phase for the received signal, for each transmitted frequency.

Each transmitting antenna 12 is designed to emit electromagnetic radiation of a set of selected frequencies partially impinging on and flowing through the material samples 16. Each receiving antenna 13 is designed to receive electromagnetic radiation emitted from any transmit antenna 12 and at least partially transmitted and reflected by the material sample 16. The receiving antenna 13 may be set up at one or more positions enabling to scan the material sample 16.

The analyser 14 acts as interface between the raw data and the user. The output of the analyser 14 consists of a three-dimensional picture of the material sample's properties as density, water contents and/or temperature.

Information about the microwave attenuation and runtime (or phase and damping of the microwave power wave) between the transmitting antennas 12 and receiving antennas 13 are calculated in the analyser 14. For each frequency of the chosen frequency set and for a chosen set of transmitting-/receiving antenna pair and at a fixed point on the material sample 16 such a calculation is performed.

In this embodiment of the invention it is assumed that the shape of the material sample 16 is known, and a three dimensional image of the material sample is stored in a memory 15 connected to the analyser 14. The three dimensional image may be used to calculate cross-sectional images for each measurement position of the material sample on the conveyor means 17. Examples of a material where the three dimensional image is known are fluids passing through the gap in a tube or samples having a defined shape, such as candy bars.

For all measurement positions along the material sample 16, the results of the damping and phase measurement, for all frequencies, are used to determine an electromagnetic picture, which is obvious for a person skilled in the art, and since this is not an essential part of the invention these steps are not disclosed in this application. The position information from the memory is saved as a three dimensional surface position data set describing the three dimensional contour of the material sample 16.

The material properties (such as water contents, density and temperature) in a material may be obtained by interpolation of the material property distributions in the following.

Assume a set of material samples has been measured previously as references. The data sets are stored in their original size or in a transformed form to reduce the data size. For these materials, the distribution of the parameters to be measured is known. These can be different temperatures, different temperature profiles, different density and water contents distributions. Extracted parameters of the measurement of these reference products form a point in a high dimensional vector space. To each point in this space a specific distribution of the parameters to be determined is associated by interpolation of the adjacent points of the reference measurements. The measurement results on an unknown product is now associated with another point on this vector space. Since the parameter distribution to be measured is known for a certain region in the vector space, the distribution associated with the measured point yields the measurement result.

On the other hand direct calculation of the material property distribution may be applied.

Figure 2:
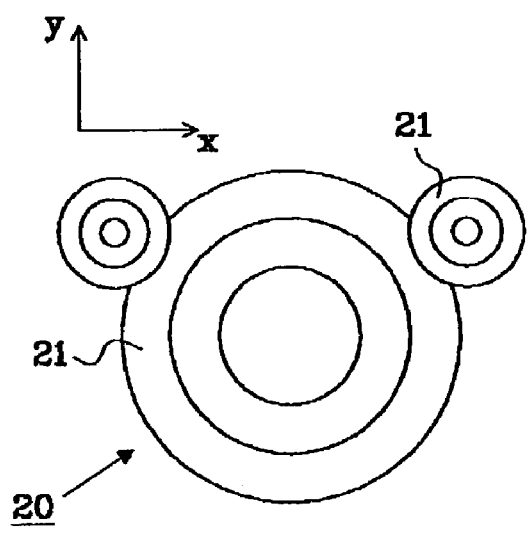
FIG. 2 is a chart indicating a dielectric model for chicken anticipated for reduction of the amount of unknown variables of the sample's dielectric behaviour.

Together with a three dimensional model of the dielectric structure of the material sample this three dimensional picture is used to determine regions within the measurement gap where the (yet unknown) dielectric function of the material can be assumed non-changing. FIG. 2 illustrates a model for chicken 20 and FIG. 3 illustrates a model for bread 30.

Each model comprises several regions 21, 31, where the dielectric function is assumed to be constant. The number of regions in the models may be adjusted, even during the process of obtaining the material properties, to obtain a smooth, but not too smooth, curve for the dielectric constant as a function of x and y co-ordinates, $\epsilon(x,y)$.

Figure 3:
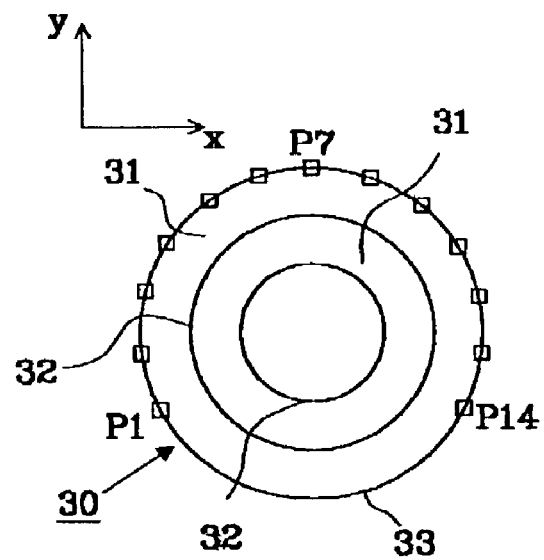
FIG. 3 is a chart indicating a dielectric model for bread anticipated for reduction of the amount of unknown variables of the sample's dielectric behaviour.

The regions in FIG. 3 are divided by concentric circles 32 and a number of mapping points P1–P14 are arranged on the outer concentric circle 33. The distance between each mapping point is preferably essentially equal.

Figure 4:
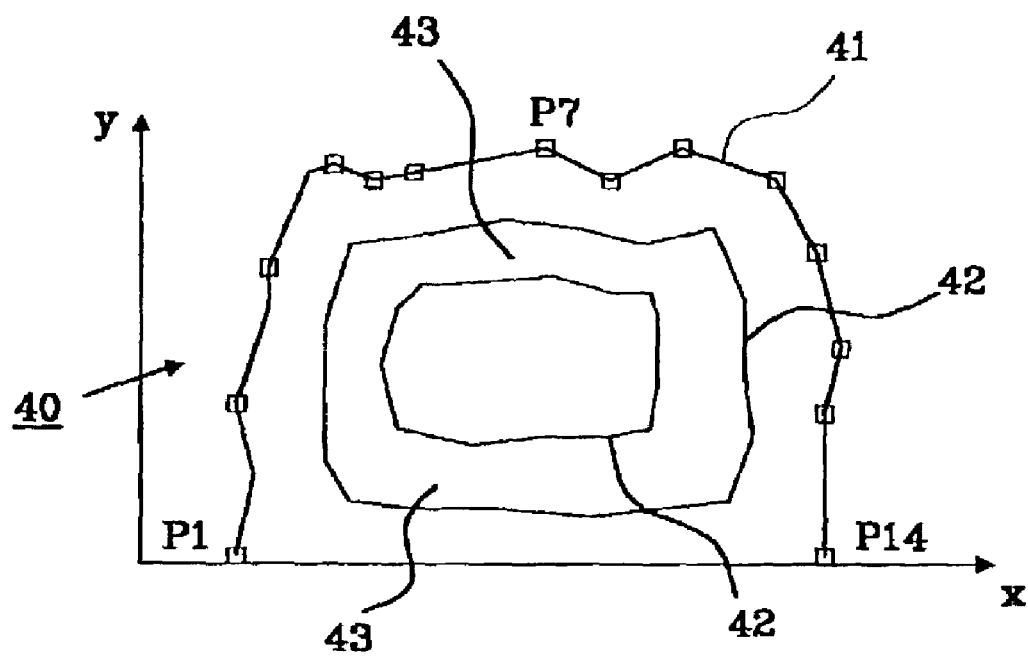
FIG. 4 illustrate a cross section of a bread loaf, where the dielectric model from FIG. 3 is mapped.

The appropriate model is adapted to the three dimensional image of the sample material, in this example a bread loaf. FIG. 4 illustrates a cross-section 40 of a three dimensional image of the bread loaf together with an x-axis and an y-axis.

The contour of the bread is indicated by the line 41, which is derived from the three dimensional surface position data set stored in the memory, and the mapping points P1–P14 in FIG. 3 are mapped upon the contour line 41. The concentric circles 32 in FIG. 3 are adjusted after the shape of the contour which is illustrated by the lines 42 in FIG. 4 divides the cross section of the bread loaf into regions 43 where the dielectric constant is assumed constant.

Below is described a simplified approach of CSI, anticipating regions where the dielectric function is constant, as indicated in the models described in FIGS. 2 and 3.

Starting with the relation between the scattered field at a given location as a function of the contrast source one can simplify the solution process considerably when the location of regions where the dielectric function is constant are known a priori:

$$u_j(p) = u_j^{inc}(p) + k^2 \int_D G(p,q) \cdot \chi(q) \cdot u_j(q) \cdot dv(q)$$

$$u_j(p) = u_j^{inc}(p) + k^2 \int_D G(p,q) \cdot \chi(q) \cdot u_j(q) \cdot dv(q)$$

$$= u_j^{inc}(p) + k^2 \sum_{n=1}^{N} \chi_n \cdot \int_{D_N} G(p,q) \cdot u_j(q) \cdot dv(q)$$

where G denotes again the two-dimensional Green's function of the electromagnetic problem $$G(p,q) = \frac{i}{4} H_0^{(i)}(k \cdot |p-q|)$$

and the polarisability $\chi_n$ depends on the dielectric function of the material $\epsilon$ being constant on the region $D_m$ and the background $\epsilon_b$ in the following way:

$$\chi_n = \frac{\varepsilon_n - \varepsilon_b}{\varepsilon_0}$$

Obviously the above step reduce the matrix size from the number of contrast sources to the number of different regions taken into account.

From the above a similar integral equation for the scattered electric field at any point r is set up.

$$F_j(r) = \frac{i}{4} k^2 \sum_{n=1}^{N} \chi_n \cdot \int_{D_n} H_0^{(i)}(k \cdot |r-q|) \cdot [F_j(q) + u_j^{inc}(q)] \cdot dv(q)$$

For this relation a similar solution process as in the general case is applied:

Below is described a calculation of the dielectric function for one pair of antennas for various frequencies for frequency independent polarisation.

Starting with the relation between the scattered field at a given location as a function of the contrast source one can simplify the solution process considerably when the location of regions where the dielectric function is constant are known a priori:

$$u(p,f) = u^{inc}(p,f) + k^2 \int_D G(p,q,f) \cdot \chi(q) \cdot u(q,f) \cdot dv(q)$$

In a step similar to the above procedure, the relation is simplified by introducing regions where the dielectric function is assumed to be constant:

$$u_j(p,f) = u^{inc}(p,f) + k^2 \sum_{n=1}^{N} \chi_n \cdot \int_{D_N} G(p,q,f) \cdot u(q,f) \cdot dv(q)$$

where G denotes again the two-dimensional Green's function of the electromagnetic problem $$G(p,q,f) = \frac{i}{4} H_0^{(i)}(k \cdot |p-q|)$$

and the polarisability $\chi_n$ depends on the dielectric function of the material $\epsilon$ being constant on the region $D_m$ and the background $\epsilon_b$ in the following way:

$$\chi_n = \frac{\varepsilon_n - \varepsilon_b}{\varepsilon_0}$$

The wave vector k is defined to be the wave propagation constant in the background medium given by $\epsilon_{r,b}$, $\mu_{r,b}$:

$$k = 2\pi f \sqrt{\epsilon_0 \mu_0 \epsilon_{r,b} \mu_{r,b}}$$

From the above a similar frequency dependent integral equation for the scattered electric field at any point r is set up.

$$F(r,f) = \frac{i}{4} k^2 \sum_{n=1}^{N} \chi_n \cdot \int_{D_N} H_0^{(i)}(k \cdot |r-q|) \cdot [F(q,f) + u^{inc}(q,f)] \cdot dv(q)$$

For this relation a similar solution process as in the general case is applied.

Below is described a calculation of the dielectric function for one pair of antennas for various frequencies for frequency dependent polarisation.

A first order approximation for the frequency dependence of the polarisation is obtained by grouping the measurement frequencies in two groups, a group at lower and a group at higher frequencies. The above summarised calculation process is repeated twice and the difference in the obtained polarisation values gives a measure for its frequency dependence.

In order to calculate the material parameters based on dielectric data, the relation between the material parameters as density, temperature and water content is needed. For most applications the following model for the temperature dependence of the dielectric function of water (extracted from experimental data published in IEEE Press 1995 by A. Kraszewski, with the title "Microwave Aquametry") is:

$$\varepsilon_{H2O}(T) = \frac{\varepsilon_\infty(T)}{1+\omega^2\tau(T)} \qquad (1)$$

Figure 5:
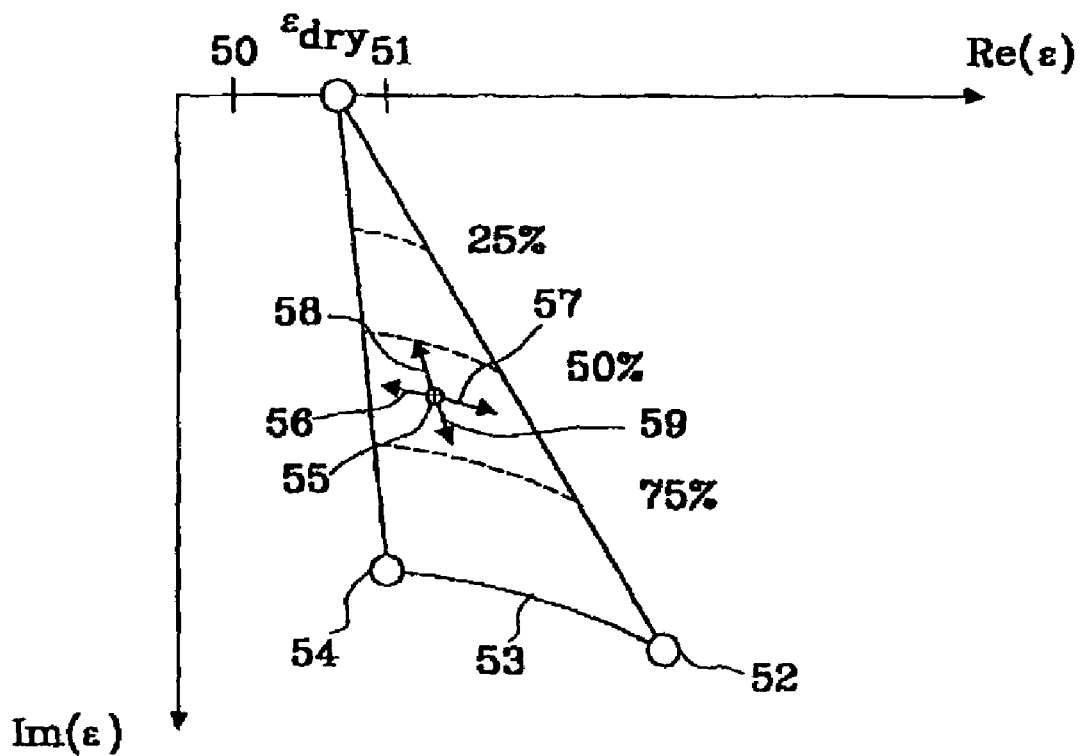
FIG. 5 is a schematic chart indicating the evaluation process in order to obtain moisture, density and temperature data from dielectric properties.

An approach (based on a simple volumetric mixing relation yields the dielectric chart depicted in FIG. 5 where the real and imaginary parts of the dielectric function are taken as independent co-ordinates:

$$\epsilon(T,c_{H2O},d) = (1-c_{H2O}) \cdot \epsilon_{basis} \cdot d + c_{H2O} \cdot (\epsilon_{H2O}(T) - \epsilon_{basis} \cdot d) \qquad (2)$$

Obviously every point in the complex dielectric plane stands for a unique water contents and material temperature when the dielectric properties of the dried base material do not change considerably. An unique density temperature plot is obtained, when the water contents is uniform.

From the spatial distribution of the dielectric function of the material sample 16, its density distribution moisture content and temperature are readily obtained applying a water model (see equation 1) and a mixing relation (see equation 2). This part of the evaluation is shown schematically in FIG. 5, a schematic view of the complete calculation process is given in FIG. 7.

The imaginary part of the dielectric constant Im($\epsilon$) forms a first axis in FIG. 5 and the real part of the dielectric constant Re($\epsilon$) forms a second axis, perpendicular to the first axis. The real part is positive and the imaginary part is negative. Any material without water content have a specific dielectric constant, so called $\epsilon_{dry}$, which vary between point 50 and 51 depending on the material, both only having a real part. On the other hand, pure water having a temperature of 4° C. has a dielectric constant 52 comprising both a real part and an imaginary part, and when the temperature of the water increase it follows a curve 53 to a point where pure water has a temperature of 99° C. and a dielectric constant 54. The real part of the dielectric constant for materials containing any amount of water decreases with higher temperature and the imaginary part of the dielectric constant for materials containing any amount of water increases with higher temperature. For illustration see the dashed lines in FIG. 5 for water content of 25, 50 and 75%.

An example of a dielectric value 55 is indicated in FIG. 5. The value 55 is situated within a region 56 delimited by the curve 53, stretching between point 52 and 54, a straight line between point 54 and $\epsilon_{dry}$ and a straight line between $\epsilon_{dry}$ and point 52. As mentioned before, if the temperature increase, with constant water content, the value of the dielectric constant 55 moves to the left in the graph as indicated by the arrow 56, and if the temperature decrease, with constant water content, the value 55 moves to the right as indicated by the arrow 57. On the other hand, if the water content decrease, with constant temperature, the value 55 moves towards $\epsilon_{dry}$ as indicated by the arrow 58, and if the water content increase, with constant temperature, the value 55 moves away from $\epsilon_{dry}$ as indicated by the arrow 59.

For each defined region 43 the calculated, or estimated, dielectric constant may be directly transformed into water content and temperature.

Figure 6:
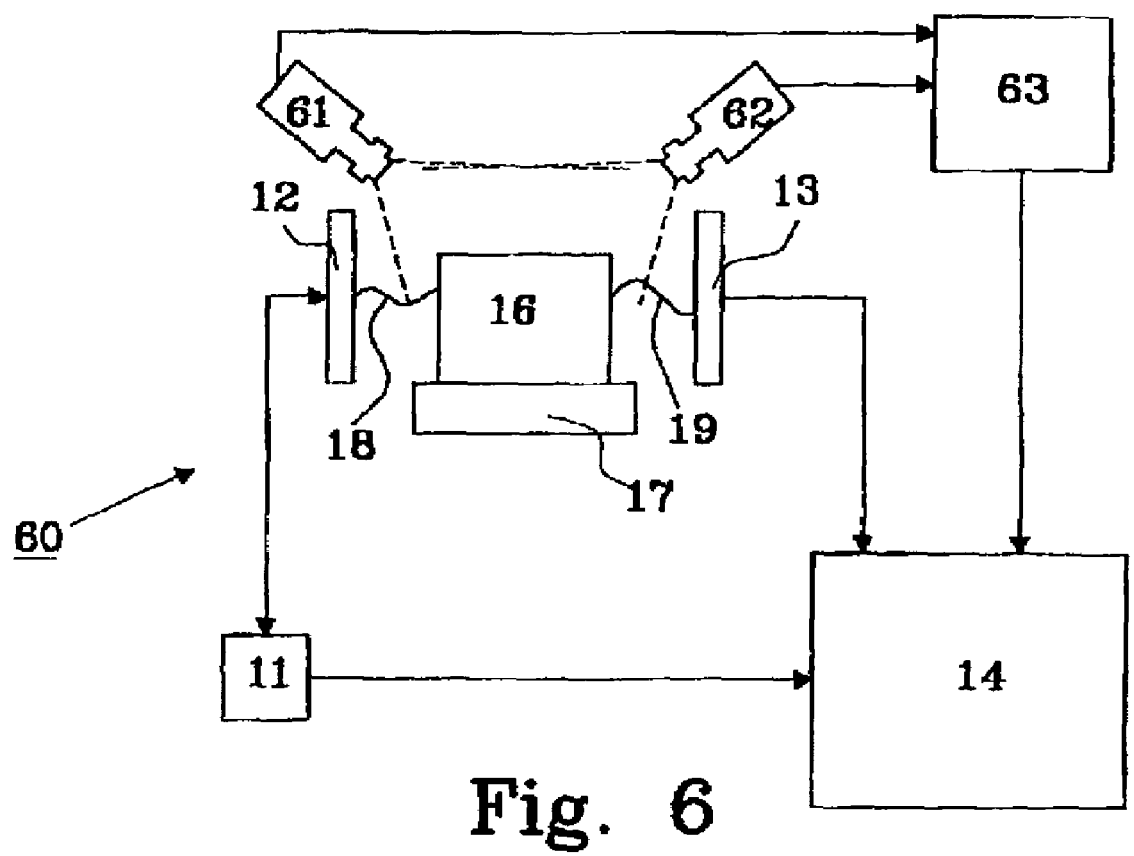
FIG. 6 is a schematic diagram of a second embodiment of a device according to this invention.

FIG. 6 illustrates a measurement device 60 according to a second embodiment of the present invention. This embodiment comprises the same parts as the first embodiment described in connection with FIG. 1, except that the memory 15 is replaced with a video imaging arrangement comprising two video cameras 61 and 62, both connected to an evaluation unit 63, which in turn is connected to the analyser 14.

Each video camera 61, 62 continuously take pictures of the material sample 16. The pictures are sent to the evaluation unit 63, where a three dimensional picture is created using known techniques. The resulting three dimensional picture similar to the one that was stored in the memory 15 in the first embodiment.

By using video imaging the system gets more flexible and it is possible to use the measurement device on material samples having an unknown shape or even a changing shape depending the water content and/or the temperature.

In the above evaluation the major reason to use video imaging is to reduce the number of unknowns in the calculation process to obtain the dielectric function's distribution in the material sample. The obtained reduction in calculation time is necessary (at least in today's available calculation power) to speed up the measurement process. In this preferred embodiment, the material samples are easily accessible to video imaging. If this is not the case, alternative solutions are ultrasound imaging. If the material samples have a simple geometric form or if subsequent material samples are very similar, no extra imaging is necessary to perform the above calculation process as described in the FIG. 1.

The calculation of the dielectric image (of a two-dimensional cross section) of the material sample in the measurement gap is accomplished by solving the previously described inverse scattering problem.

Both video cameras 61 and 62 image the part of the measurement gap. The location of the cameras 61 and 62 are chosen in a way to enable the reconstruction of a three-dimensional picture where the material sample 16 is positioned within the measurement gap.

For each position of the material sample 16 a three-dimensional picture of the sample location in the measurement gap is calculated based on images taken by the video cameras 61 and 62.

In addition the position information contained in the optical image is used together with a priori knowledge of the material structure the obtain a first guess of the dielectric structure under measurement. This enables to reduce the number of unknowns of the dielectric imaging calculation process drastically (about two orders of magnitude) and to speed up the calculation considerably.

Figure 7:
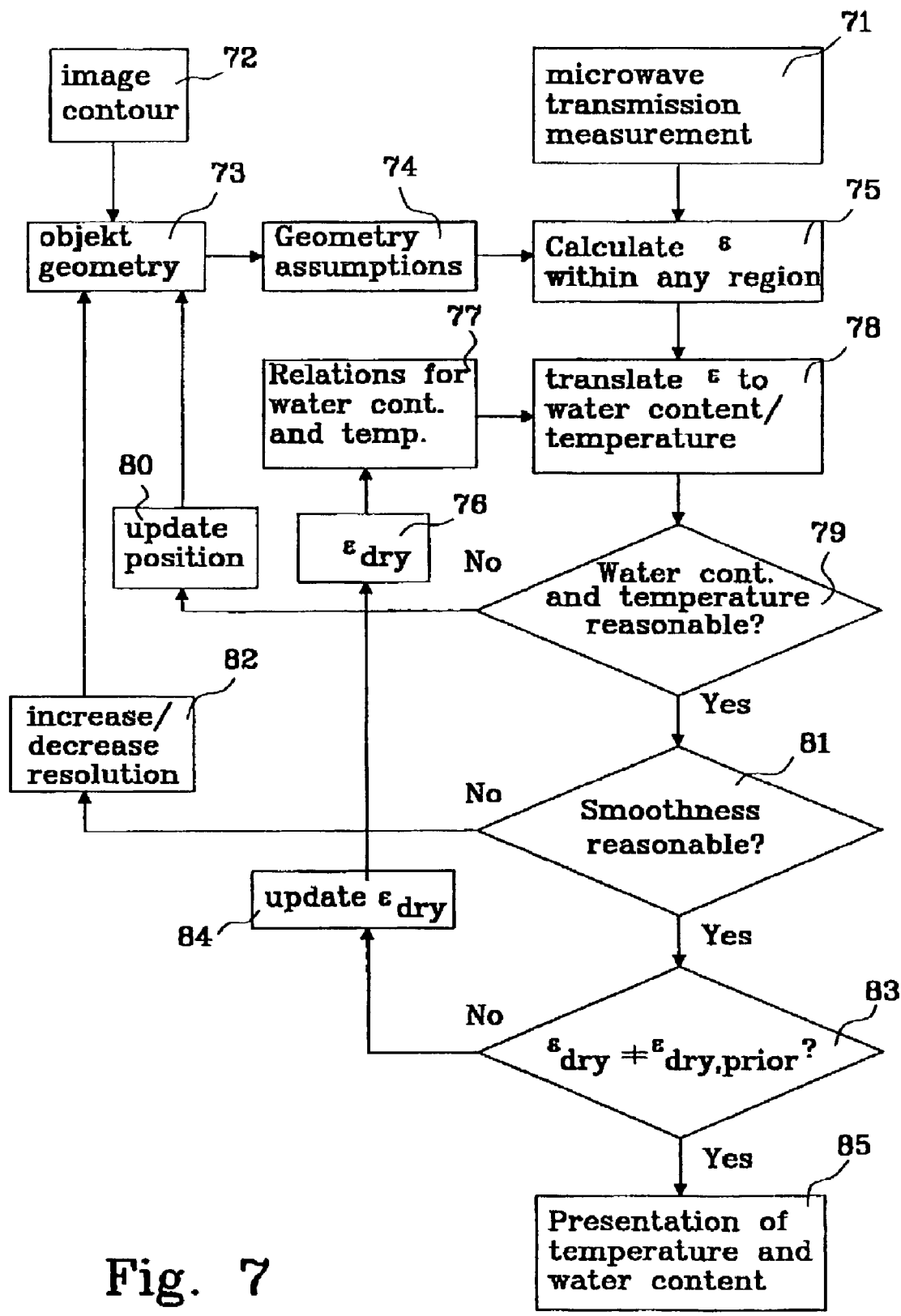
FIG. 7 is a flow chart of the whole calculation process.

FIG. 7 show a schematic view of the complete calculation process for the device according to the invention.

As previously described in connection with FIG. 1 and FIG. 6, the input data to the analyser comprises the microwave transmission measurements, i.e. information regarding the emitted signals 18 (amplitude and phase for each used frequency) and the detected signals 19 (amplitude and phase for the corresponding frequency). This information is input in the calculation process, 71.

Information regarding the image contour of the material sample 16 is also needed and inputted into the process, 72. A predetermined resolution of the image contour is used to start the calculation process. The resolution may be increased or decreased dependent on the calculation results, as described below. Information regarding the position of the material sample 16 in the measurement gap is also inputted into the process in 72.

The information from 72 is used to establish an object geometry, 73. A model, for instance as described in FIG. 3, is thereafter used to determine regions wherein the dielectric function is assumed of the first order, i.e. constant. The number of regions used is set in the model. The selected model, in this case model 30, is used to establish regions in the material sample 16 by adjusting the concentric circles to the result of the object geometry from 73, which is done in 74, as described in FIG. 4.

The geometry assumptions from 74 and the result from the microwave transmission measurement from 71, is thereafter used to calculate the dielectric constant within each region, 75. The calculation process have previously been described in this application.

Another piece of information is needed to convert the dielectric constant into water content and/or temperature, that is the dielectric constant for the material sample 16, when there is no water content in the material, $\epsilon_{dry}$. This information may be obtained from literature or from previously made measurements on similar material samples, 76.

This information is used to establish the equations defining the relation between the dielectric constant and the water content and temperature, as described in connection with FIG. 5, 77.

The resulting dielectric constant within each region from 75 is thereafter translated (or converted) into water content and temperature, 78.

If the calculation process is well established the following steps may be unnecessary, but in most cases they are necessary to avoid unreasonable results.

In 79, a check is made to determine if the resulting temperature and water contents are reasonable, i.e. the temperature is greater than zero, T>0, the water content is greater than zero, $C_{H2O}>0$ (i.e. Im($\epsilon$)<0) and if the water content is less than 100%, $C_{H2O}<100\%$.

If any of the above mentioned checks does not pass, the calculation process is fed back via 80, where the position of the material sample is updated. If video cameras are used, as described in FIG. 6, a new image contour of the material sample is used to repeat the steps 74, 75 and 78. In the case where the image contour information is previously stored in a memory, as described in FIG. 1, the calculation process may make a small adjustment to the material size, deform the material contour, translate the material in one direction and the repeat steps 74, 75 and 78.

If no objections are raised regarding reasonable results in 79 the process continue to 81, where the smoothness of the curve describing the dielectric function across the cross section of the material sample is investigated. If the dielectric function is too smooth or not enough smooth, the process is fed back via 82, where the resolution of the image contour is changed. Thereafter the steps 73, 74, 75 and 78 are repeated before the checks 79 and 81 are performed again.

There is also a possibility to change the number of regions in the used model in 74 to increase or decrease the number of regions to calculate.

If the smoothness of the curve is acceptable, the process proceed to 83, where a new dry dielectric constant, $\epsilon_{dry}$, of the material is calculated depending on the calculated results in the process. If the calculated dry dielectric constant, $\epsilon_{dry}$, does not correspond with the used dry dielectric constant, $\epsilon_{dry,prior}$, the dielectric constant is updated in 84 and the translation of the dielectric function in step 76, 77 and 79 are repeated, before the checks 79, 81 and 83 are performed again.

If no objections are raised in 83, the process presents the results in the form of water content and or temperature at step 85.

The calculation process described in FIG. 7 is normally performed for a position of the material sample in the measurement gap. When the calculation process is completed the conveyor means 17, on which the material sample 16 is moved to a new position where another measurement is performed. The updated information, regarding, $\epsilon_{dry}$, number of regions, position of material, and so on, are used at the next position to speed up the process.

In a further embodiment of the present invention a multiple of receiving antennas may be used to allow a single processing as described in FIG. 7, to establish the three dimensional temperature, or water content, distribution within the material sample.

The calculation process in FIG. 7 only describe the embodiment where the model is used to establish regions, where the dielectric constant is assumed constant.

The invention claimed is:

1. A device for measuring the distribution of selected properties of a material arranged on a conveyor, said device comprising:
   an emitter of electromagnetic radiation arranged at one side of said conveyor, said emitter emitting electromagnetic radiation in a multiple of frequencies in a selected frequency range towards said material;
   at least a sensor arranged on an opposite side of said conveyor, compared to said emitter, said sensor detecting electromagnetic radiation in said selected frequency range being emitted from said material, said electromagnetic radiation originating from said emitter;
   an analyser arranged to receive information regarding said emitted electromagnetic radiation and said detected electromagnetic radiation, said information comprising amplitude and/or phase for each selected frequency, said analyser being arranged to calculate the selected property distribution in said material based on the received information;
   an image device arranged to send information to said analyser to create a three dimensional contour of the material, said image device includes at least one imaging sensor connected to an image processing device, said at least one imaging sensor detecting an image of said material, which is processed into a three-dimensional contour of said material in said image processing device,
   wherein said at least one imaging sensor detects a picture of the reflectivity in optical wavelengths.

2. The device according to claim 1, wherein said at least one imaging sensor is a video camera.

3. A device for measuring the distribution of selected properties of a material arranged on a conveyor, said device comprising:
   an emitter of electromagnetic radiation arranged at one side of said conveyor, said emitter emitting electromagnetic radiation in a multiple of frequencies in a selected frequency range towards said material;
   at least a sensor arranged on an opposite side of said conveyor, compared to said emitter, said sensor detecting electromagnetic radiation in said selected frequency range being emitted from said material, said electromagnetic radiation originating from said emitter;
   an analyser arranged to receive information regarding said emitted electromagnetic radiation and said detected electromagnetic radiation, said information comprising amplitude and/or phase for each selected frequency, said analyser being arranged to calculate the selected property distribution in said material based on the received information;
   an image device arranged to send information to said analyser to create a three dimensional contour of the material, said image device includes at least one imaging sensor connected to an image processing device, said at least one imaging sensor detecting an image of said material, which is processed into a three-dimensional contour of said material in said image processing device, wherein said at least one imaging sensor detects a picture of the reflectivity and transmissivity and propagation speed of sound waves.

4. The device according to claim 3, wherein said at least one imaging sensor is an ultrasound imaging device.

5. The device according to claims 1 or 3, wherein said analyser includes means for interpolating previously measured results, stored in a memory, to obtain the selected property distribution in said material.

6. The device according to claim 1 or 3, wherein said analyser includes means for calculating the dielectric distribution in said material and converting said dielectric distribution into the selected property distribution in said material.

7. The device according to claim 6, wherein said means for calculating the dielectric distribution comprises a three dimensional model determining regions within said material where the dielectric function is assumed non-changing, and means for applying said model to said three dimensional contour of the material, whereby a dielectric distribution is obtained.

8. The device according to claim 6, wherein further comprising means for converting said dielectric distribution into the selected property distribution.

* * * * *